United States Patent [19]
Vergano

[11] Patent Number: 5,885,204
[45] Date of Patent: Mar. 23, 1999

[54] INCONTINENCE DEVICE AND METHOD OF USE

[75] Inventor: Michael G. Vergano, Cumberland, R.I.

[73] Assignee: Insight Medical Corporation, Bolton, Mass.

[21] Appl. No.: 757,810

[22] Filed: Nov. 27, 1996

[51] Int. Cl.[6] ............................................. A61F 2/00
[52] U.S. Cl. ................................. 600/29; 128/DIG. 25
[58] Field of Search ................. 600/29–32; 128/DIG. 25

[56] References Cited

U.S. PATENT DOCUMENTS

| | | | |
|---|---|---|---|
| 3,340,876 | 9/1967 | Hill . | |
| 3,349,768 | 10/1967 | Keane | 165/65 |
| 3,512,185 | 5/1970 | Ellis . | |
| 3,661,155 | 5/1972 | Lindan | 128/295 |
| 3,683,914 | 8/1972 | Crowley | 128/285 |
| 3,705,575 | 12/1972 | Edwards | 128/1 R |
| 3,776,235 | 12/1973 | Ratcliffe et al. | 128/295 |
| 3,958,564 | 5/1976 | Langguth | 128/2.06 E |
| 3,995,329 | 12/1976 | Williams | 4/110 |
| 4,194,508 | 3/1980 | Anderson | 128/295 |
| 4,198,979 | 4/1980 | Cooney et al. | 128/295 |
| 4,256,093 | 3/1981 | Helms et al. | 128/1 R |
| 4,421,511 | 12/1983 | Steer et al. | 604/329 |
| 4,484,917 | 11/1984 | Blackmon | 604/327 |
| 4,496,355 | 1/1985 | Hall et al. | 604/327 |
| 4,563,183 | 1/1986 | Barrodale et al. | 604/329 |
| 4,568,339 | 2/1986 | Steer | 604/329 |
| 4,626,250 | 12/1986 | Schneider | 604/352 |
| 4,690,677 | 9/1987 | Erb | 604/329 |
| 4,759,354 | 7/1988 | Quarfoot | 128/156 |
| 4,767,411 | 8/1988 | Edmunds | 604/180 |
| 4,795,449 | 1/1989 | Schneider et al. | 604/329 |
| 4,822,347 | 4/1989 | MacDougall | 604/329 |
| 4,846,819 | 7/1989 | Welch | 604/629 |
| 4,889,532 | 12/1989 | Metz et al. | 604/330 |
| 4,904,248 | 2/1990 | Vaillancourt | 604/329 |
| 5,074,855 | 12/1991 | Rosenbluth et al. | 604/385 |
| 5,090,424 | 2/1992 | Simon et al. | 128/885 |
| 5,131,906 | 7/1992 | Chen | 600/29 |
| 5,195,997 | 3/1993 | Carns | 604/347 |
| 5,263,947 | 11/1993 | Kay | 604/331 |
| 5,336,208 | 8/1994 | Rosenbluth et al. | 604/329 |

FOREIGN PATENT DOCUMENTS

| | | | |
|---|---|---|---|
| 947602 | 5/1974 | Canada | 128/110 |
| 1223353 | 6/1960 | France . | |
| 2542995 | 9/1984 | France | A61F 5/44 |
| 2817571 | 10/1978 | Germany | A61F 5/44 |
| 3633824A1 | 4/1988 | Germany | A61F 5/43 |
| 1467144 | 3/1977 | United Kingdom | A61F 5/44 |
| 2193438 | 2/1988 | United Kingdom | A61F 5/455 |
| WO90/08561 | 8/1990 | WIPO | A61M 1/00 |
| WO96/39989 | 12/1996 | WIPO | A61F 2/00 |
| WO96/39991 | 12/1996 | WIPO | A61F 2/00 |

OTHER PUBLICATIONS

Neurology and Urodynamics, vol. 15, No. 1, 1996, pp. 381–382.

*Primary Examiner*—John P. Lacyk
*Attorney, Agent, or Firm*—Wolf, Greenfield & Sacks, P.C.

[57] ABSTRACT

An improved urethral cap for alleviating urinary incontinence when positioned on the body of the user is provided. The improved urethral cap includes a body portion defining an interior chamber, the chamber providing a vacuum therein to hold the urethral cap in contact with the body of the user. The cap further includes at least one flange supported by the body portion, the flange having a thickness of less than 0.75 millimeters, and preferably less than 0.5 millimeters. The improved urethral cap has increased flexibility and therefore provides increased comfort to a user when in place over the urethra.

22 Claims, 6 Drawing Sheets

INCONTINENCE DEVICE AND METHOD OF USE

TECHNICAL FIELD

The present application relates to a urethral cap for treatment of urinary incontinence in females, and more particularly to an improved urethral cap which fits a female more comfortably.

BACKGROUND OF RELATED ART

Urinary incontinence, such as stress incontinence, in females is a substantial problem throughout the world. A variety of mechanisms have been suggested for use to alleviate the condition which can be a social as well as medical problem for those so afflicted.

Many suggested medical devices to alleviate urinary incontinence in females require the use of internal components such as catheters, balloons, pessary or the like which pass into the urethra and are positioned within the body in use. Such internal components can be a source of irritation to the body, thereby causing discomfort to the user and, in some cases, can result in an unwanted body reaction, such as an infection. In addition, such devices as are known, can be expensive and/or inconvenient to use and transport for use.

More recently, a urethral cap has been used for alleviating urinary incontinence, which cap overcomes many of the afore-mentioned problems associated with conventional medical devices. In use, the urethral cap is positioned exterior to the body and utilizes atmospheric pressure to create a vacuum in order to maintain the cap in position on the body of the user. The cap has been shown to be helpful in many cases to alleviate urinary incontinence in females, thereby providing the user with an inexpensive device which is easy to transport, simple to apply and remove and which is unlikely to cause infection in the user when properly used.

In order to provide the user with a device resistant to collapse or deformation by atmospheric pressure, previous designed urethral caps were provided with walls of certain thickness. While providing a comfortable fit for many women, the predetermined thickness decreased the flexibility, i.e. the compliance or softness of the device, thereby sometimes causing discomfort, and hence irritation, in some women. In addition, previously designed caps often included a generally circular flange which has also been found to cause discomfort in some user due to its geometric configuration.

There is therefore needed an improved urethral cap which provides increased comfort to a wide range of users while maintaining the integrity of the device.

SUMMARY

An improved urethral cap for alleviating urinary incontinence when positioned on the body of the user is provided. The cap includes a body portion defining an interior chamber, the chamber providing a vacuum therein to hold the urethral cap in contact with the body of the user. The cap further includes a single flange which is supported by the body portion and which includes a body contacting surface. The single flange acts as a sealing surface when the flange encircles the urethra of the user such that movement of the body of the user adjacent the flange causes corresponding movement of the flange while maintaining a seal around the urethra.

In one embodiment the urethral cap includes at least one flexible flange supported by a gripping portion, the at least one flange having a body contacting surface to act as a sealing surface with the body of the user, the urethral cap also including a strengthening ridge disposed at least partially about and supported by the at least one flange. The strengthening ridge provides support to the at least one flange when in place over the urethra while allowing the flange to remain flexible.

In another embodiment the urethral cap includes at least one flange supported by a gripping portion, the at least one flange having a thickness of less than approximately 0.4 millimeters to provide the flange with pliability that closely approximates the pliability of the surrounding tissue.

In yet another embodiment the urethral cap includes a concave body contacting surface, an outwardly extending flange having a shape selected from the group consisting of a generally elliptical shape and an egg shape, the flange having a thickness of less than approximately 0.5 millimeters and a strengthening ridge disposed about the flange to provide support thereof. The elliptical and/or egg shape are provided in order to conform to the anatomy of the user.

In another embodiment the urethral cap includes a single flange extending from the body portion and having a continuous curvature and an elongated configuration constructed and arranged to align with the natural contours of a woman between the labia and extending from the vagina to the clitoris for increased comfort.

A method for positioning a female incontinence device over the urethra of a user is also disclosed. The method includes providing a body portion, supporting an outwardly extending flange from the body portion, the flange having a thickness of less than approximately 0.4 millimeters; applying a sealing material to one side of the flange; grasping the body portion; manipulating the flange between the labia and over the urethra; contacting the sealing material with the area surrounding the urethra while depressing the body portion; and releasing the body portion.

The improved urethral cap embodiments alleviate urinary incontinence, provide increased comfort to a wide range of users, are easily applied and taken off and may be worn for extended periods of time, as required. In addition, the improved caps are relatively inexpensive to manufacture.

BRIEF DESCRIPTION OF THE DRAWINGS

Various embodiments are described herein with reference to the drawings, wherein.

DETAILED DESCRIPTION OF THE PREFERRED EMBODIMENTS

Figure 1:
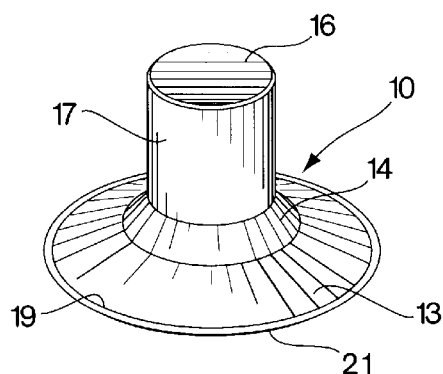
FIG. 1 is a perspective view of a first embodiment of the urethral cap in accordance with this invention.
Figure 2:
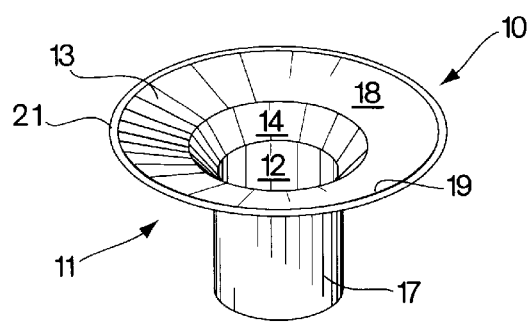
FIG. 2 is a perspective view of the embodiment of FIG. 1, rotated 180 degrees.

Referring initially to FIGS. 1 and 2, a first preferred embodiment of a urethral cap or incontinence device is illustrated at 10. The cap includes a body 11 defining an interior chamber 12 and includes a gripping portion 17, an outer flange 13 and an intermediate flange 14. In the present embodiment, intermediate flange 14 extends at an angle from gripping portion 17 and has a decreasing thickness as the flange 14 extends from gripping portion 17 to outer flange 13. Outer flange 13 extends from intermediate flange 14, is preferably of constant thickness, preferably includes a thickened ring, or bead 21 disposed along an outer edge 19 thereof and also includes a body contacting surface 18, as described in greater detail hereinbelow.

Body 11 defines an interior chamber 12 which provides cap 10 with sufficient interior space that extends from gripping portion 17 to the tip of the intermediate flange 14. The interior space provides at least a partial vacuum in the interior chamber when cap 10 is compressed by the finger of the user, the interior space also allowing resilient rebound during positioning of urethral cap 10.

The gripping portion 17 of the urethral cap in the preferred embodiment of FIG. 1 includes a generally cylindrical wall 15 disposed around a central, vertical, longitudinal axis "Y" of cap 10, the cylindrical wall being capped at a first end thereof, by an outer end wall 16 perpendicular to axis "Y" and supporting intermediate flange 14 at a second end thereof, opposite the first end. The cylindrical wall 15 and end wall 16 of the cap combine to provide the user with a gripping portion 17 in order to allow the user to easily position the urethral cap on the body and to facilitate manipulation and removal of the urethral cap therefrom by the fingers of the user.

Figure 3:
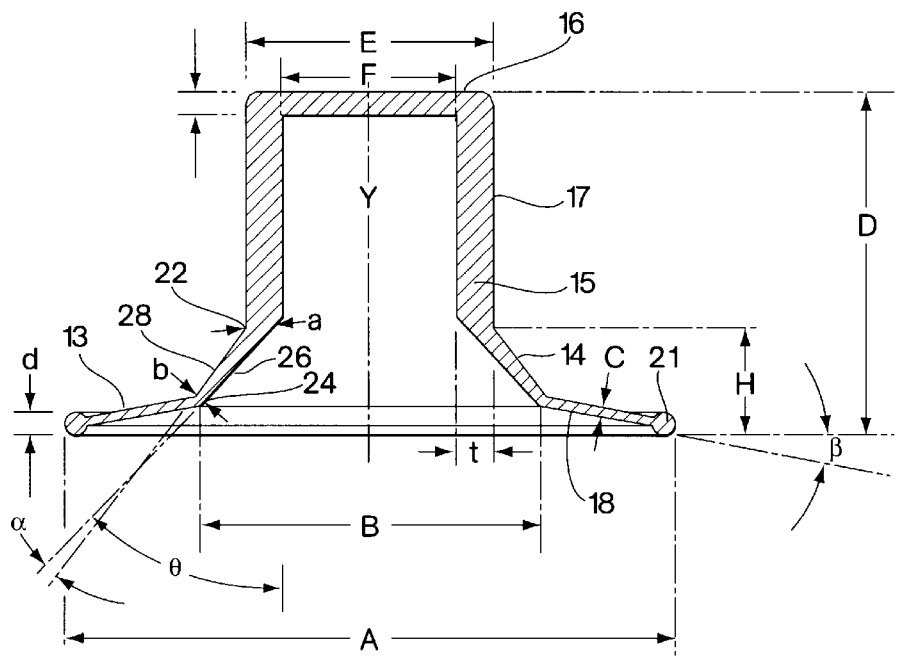
FIG. 3 is a cross-sectional, side view of the embodiment of FIG. 1.
Figure 4:
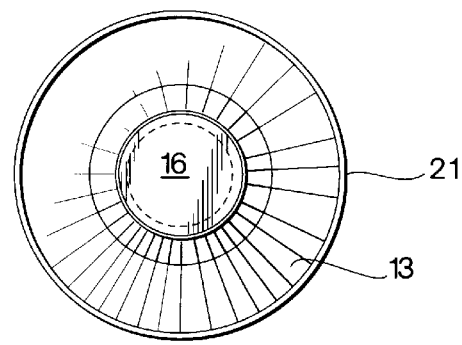
FIG. 4 is a top view of the embodiment of FIG. 1.

Referring now to FIG. 3, a cross-sectional view of the urethral cap 10 of the embodiment of FIG. 1 is illustrated. As shown in FIG. 3, the cylindrical wall thickness, "t", is configured to resist collapse and/or significant deformation. The thickness, "t" of wall 15 can be, for example, approximately 2 millimeters with a preferred range of 1.5 to 3 millimeters. Although the cap is shown as having a cylindrical shaped side wall 15, wall 15 can be any number of shapes and sizes as long as gripping by the user is facilitated while structural integrity of the cap is maintained.

With continuing reference to FIG. 3, intermediate flange 14 includes an inner wall surface 26 adjacent to lower portion of inner chamber 12 and an outer wall surface 28, opposite the inner surface. Flange 14 is preferably concentric about axis Y, is frustoconical in shape and is preferably disposed at an angle θ, measured from the inner wall surface with respect to axis "Y". In the present embodiment θ is approximately 45°, but may be anywhere in the range of approximately 20 to 135 degrees.

In the present embodiment, first end 22 of flange 14 has a thickness, "a", approximately equal to the thickness "t" of wall 15, or approximately 2 millimeters for the present embodiment. As intermediate flange 14 extends outwardly, or away from wall 15 to outer flange 13, the thickness of intermediate flange 14 decreases until the thickness, "b", of second end 24 of flange 14 is approximately equal to the thickness of outer flange 13, or approximately 0.38 millimeters in the present embodiment. As shown in FIG. 3, angle α, which is the angle between inner wall surface 26 and outer wall surface 28, also represents the thickness of flange 14 at "b". The thickness of the urethral cap is arranged so that wall 15 has a thicker section and is more resistant to collapse or deformation by atmospheric pressure than is the tapered, intermediate flange portion 14. The thickness of intermediate flange 14 is dependant upon the thickness of wall 15 and the thickness of outer flange 13 therefore, as the thickness of the wall and outer flange may vary, so may the thickness of intermediate flange 14. Although flange 14 is described as having a tapered configuration it may be beneficial, in some instances, for the thickness of intermediate flange 14 to remain constant, as long as intermediate flange 14 helps provide closure of the meatus when cap 10 is in place while providing the user with a comfortable fit.

With continued reference to FIG. 3, outer flange 13 has a reduced thickness, is supported by flange 14 and extends at an angle β. Flange 13 also preferably includes a continuous, encircling, cylindrical cross section ring or bead 21 disposed along an outer edge 19 thereof and also includes a body contacting surface 18. In the present embodiment β is defined from the x-axis and is approximately 8°, but may be anywhere in the range of approximately 70 to-55 degrees with respect to the x-axis. Outer flange 13 preferably has a constant thickness, "C", of approximately 0.38 millimeters, with a preferred range of 0.125 to 0.75 millimeters for the present embodiment. Bead 21 preferably has a thickness, "d", of approximately 1 millimeters, with a preferred range of 0.5 to 2 millimeters. Bead 21 is continuous and is disposed along outer edge 19 in the present embodiment, but may alternately be non-continuous and may be disposed anywhere along flange 13. The thickness of bead 21 provides additional support and tear resistance for flange 13, along the outer edge thereof in the embodiment of FIG. 1, while maintaining the increased flexibility of flange 13 due to the thin construction of the outer flange. Body contacting surface 18 preferably forms a continuous ring about the opening or meatus of the urethra of the body of the female user. However, other portions of the cap can be square, round, oblong, bulbous, or of any shape desired.

Figure 6:
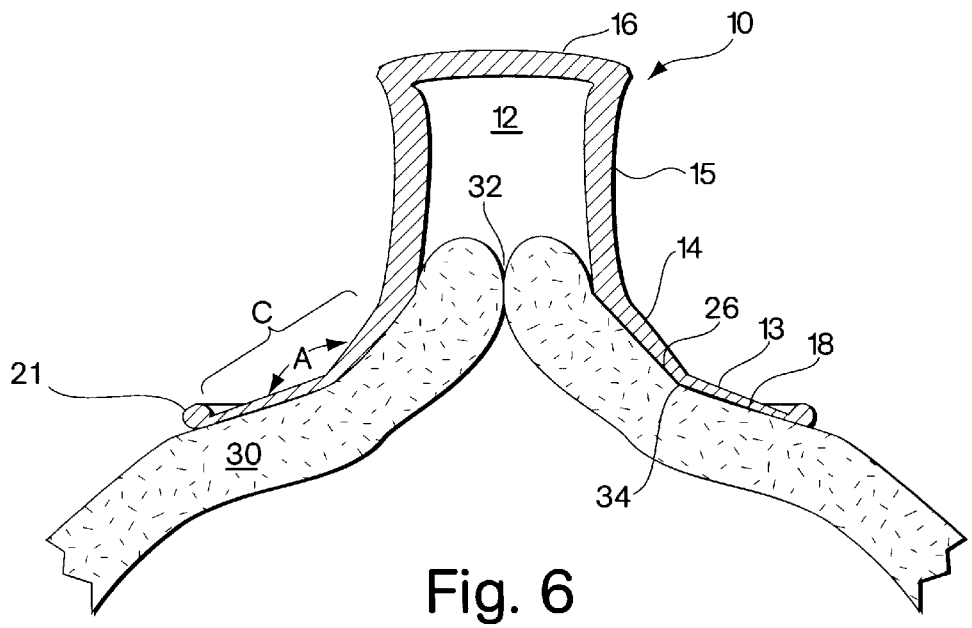
FIG. 6 is a diagrammatic cross-sectional side view of the urethral cap of FIG. 1 in contact with the urethra of the user.

As best seen in the cross section of FIG. 6, the flange 13 is deformable towards or closely contacts the body 30 at the planar area of the body surrounding the meatus or urethra orifice 32. A portion of the urethra indicated at 34 can be drawn into contact with the flange 13 and the inner wall surface 26 of intermediate flange 14, which acts to close the meatus in order to maintain the position of the cap, to form a good seal with the body at flange 13 and to close the meatus to urine flow, as described in greater detail hereinbelow. By providing intermediate flange 14 with a tapered thickness and flange 13 with a relatively thin, continuous thickness, "c", the flexibility of flange 13 and flange 14 is without compromising the structural integrity of cap 10. The thinness of flange 13 increases the comfort of the device when applied to the user because the pliability of flange 13 closely approximates the pliability of the tissue 34 with which it is in contact. Thus, as the user moves, the body contacting surface 18 is flexible enough to move with the tissue 34 it contacts, without compromising the suction which adheres the device to the user, or the structural integrity.

The urethral cap is preferably integrally formed as by conventional molding techniques, but can alternately be made by dipping, spraying or other techniques. The material of the integral cap is preferably silicone rubber, and is most preferably an FDA approved medical grade. However, other elastomeric materials such as elastomeric urethanes, polyvinyl chlorides, natural and other rubbery material or synthetic polymeric materials can be used. In the preferred embodiment a silicone blend by weight of approximately 10% Dow Silicon HS-30 and 90% Dow Silicone #4-2903, both of which are manufactured by Dow-Corning Corp. of Midland, Mich. The mixture preferably has a Durometer Shore A of 10, tensile strength of 90 psi and an elongation of 515%. The mixture is preferably cured with a conventional peroxide curing agents such as VAROX® DBPH-50 cure, a product of R.T. Vanderbilt Company of Norwalk, Connecticut or Lupersol 101, a product of Penwalt Corp. of Buffalo, N.Y., both of which are liquid difunctional peroxides of high thermal stability. Conventional FDA approved colorants can be used to add color as, for example, E-4592 colorant, a product of Akrochem Corp. of Akron, Ohio, or alternatively, other organic and inorganic pigments.

In some cases, the body need not be integrally formed but can be formed of other materials which can be polymeric or metallic. In these cases, at least a portion of the body opening into the interior chamber 12 is formed of a resilient material which can be elastically and reciprocally moved by the fingers from the at rest position as shown in FIG. 3 to a compressed or reduced chamber position and then allowed to expand to the at rest position. This is necessary in order to provide at least a partial vacuum in the chamber to seal the cap to the body by an air pressure differential between the air within the chamber and the atmospheric air pressure as will be described.

The dimensions of the urethral cap can vary greatly. However, consistent with normal anatomy of females in the United States, it is preferred that the diameter A be in the range of approximately 2.0 to 3.5 centimeters and with approximately 3 centimeters being used in the preferred embodiment. Diameter B is preferably in the range of approximately 1 centimeter to 2 centimeters with approximately 1.7 centimeters being preferred. The height D of the device is preferably approximately 1 to 2 centimeters and in the preferred embodiment is approximately 1.65 centimeters. This height can vary greatly but by maintaining the device approximately 1 to 2 centimeters in height, the device can be worn without discomfort, positioned easily and is resistant to dislodging by garments worn by the user.

Distance E, which is the diameter of cap end wall 16 can be, for example, 1.27 centimeters in the preferred embodiment with the diameter of chamber 12 shown at F being 0.86 centimeters in the preferred embodiment. Distance H which defines in part the interior chamber can be 4.75 millimeters in the preferred embodiment but again can vary greatly. The most important dimensions, other than the thickness of flanges 13 and 14, relate to the range of 2.0 to 3.5 centimeters for outer diameter A, of flange 13, to ensure proper positioning in the body and preferably the height of the device is no more than about 2 centimeters to allow ease of use and reuse.

In use, the meatus is preferably closed by a gentle compression of the area around the meatus by the urethral cap, to form a closure maintained in position by an air pressure difference. In order to provide an air and liquid seal between the skin of the body and the flange, a sealant material which can be adhesive, but need not be an adhesive, is preferably applied to the body contacting surface 18, prior to the positioning of the cap. If the seal is adhesive, it not only seals against air and liquid pressure leakage, but can also act to hold the device in contact with the body. However, it is preferred not to use an adhesive as the body adhering portion since this could be irritating to the body if sufficient adhesive is used to provide proper protection. On the other hand when substantially no adhesive properties are used in the sealing material, sufficient protection against urinary leakage is provided by the incontinence device 10 of this invention.

The sealing material (not shown) can be known adhesives which are substantially nonirritating to the body and can be used in contact with the body over a period of time. Such adhesives include the water soluble paste FIXADENT® or CONFIDENT an adhesive produced by Block Drug of Jersey City, N.J. However, sealing materials which are non-adhesive such as AQUAPHOR® healing ointment and AQUAPHOR® original formula which are available from Beiersdorf, Inc. of Norwalk, Conn., can also be utilized. Other conventional lubricants including petrolatum or petroleum jelly such as Vaseline® can also be utilized. The sealing material compensates for irregularities in the skin or cap sealing surface flange and thus provides for protection against air and urine leakage in use of the device when the device is applied to the body.

The sealing material can be applied by the user using a Q-tip applicator or the fingertip to rub the sealing material or adhesive over the body sealing surface just prior to use. In some cases, the lubricant or adhesive can be prepositioned on the device with a cover or release strip applied thereover to prevent sticking or removal of the sealant or adhesive prior to application. In some cases, a plurality of sealant and cover strips can be used, as desired. In the preferred embodiment, the sealant material is applied just prior to use by the user as when AQUAPHOR® ointment is used.

Figure 5:
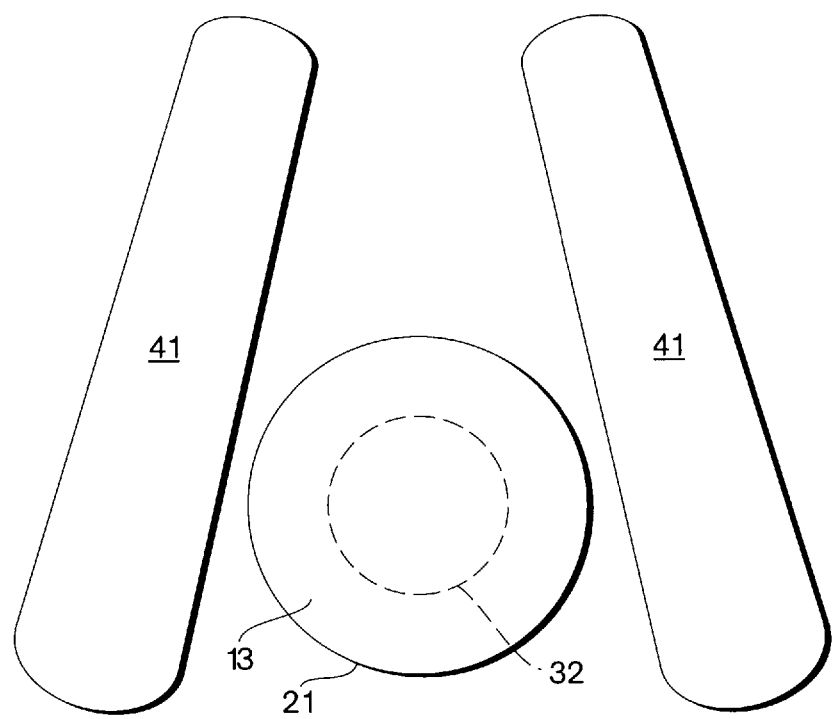
FIG. 5 is a semi-diagrammatic top plan view of the urethral cap of FIG. 1 during positioning on the body of the user.
Figure 7:
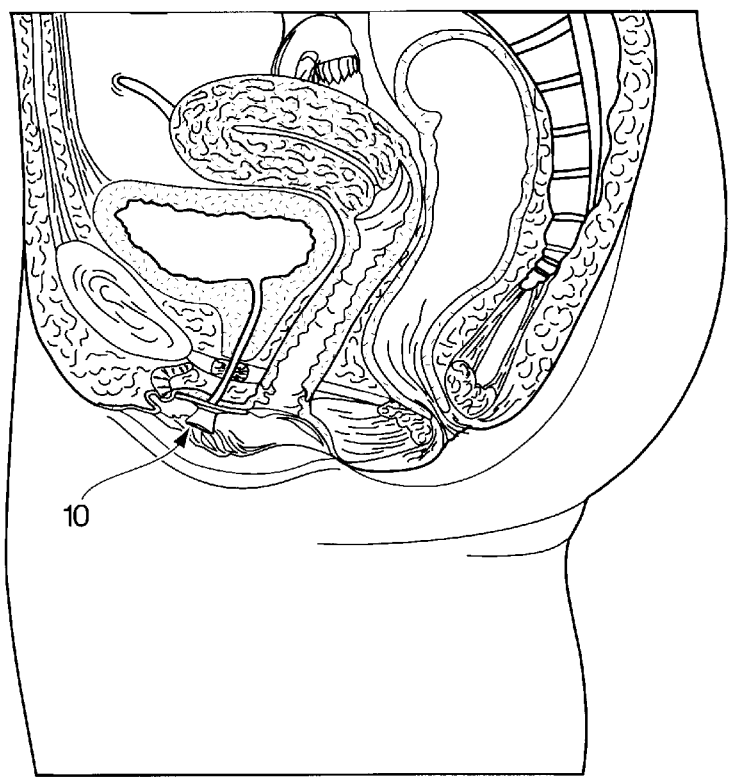
FIG. 7 is a diagrammatic cross-sectional side view of the lower extremities of a user with the urethral cap in place.

FIGS. 5–7 diagrammatically show placement on the body. In FIG. 5, the labia 41 are diagrammatically illustrated with the urethral opening or meatus being shown within area 32, with the flange 13 and bead 21 positioned thereover. In FIG. 6, the cap 10 is shown in position with the skin of the body about the meatus pulled into direct contact with the body contacting surface 18 of the flange and the inner wall surface 26 of intermediate flange 14. This closes the urethral orifice and the positioning of the skin below the flange acts to aid in centering and maintaining the cap in position on the body as well as to prevent urine outflow. Similarly, because the flange 13 is positioned to lie substantially just within the labia 41 at a planar area around the meatus, positioning is maintained and this spacing aids in locating and placing the urethral cap in position.

In the method of applying the urethral cap of this invention, the cap is deformed inwardly by the fingers of the user and then applied to the orifice of the urethra and allowed to expand to its original shape as shown in FIG. 3. This creates a vacuum within the inner chamber 12 causing outside atmospheric pressure to push against the outer flange 13 and intermediate flange 14 to maintain the urethral cap in good sealing engagement with the body. The skin or tissue immediately surrounding the meatus is compressed by the air pressure difference and a seal is formed with the cap 10 at the surface 34. The sealing material preapplied to the body contacting surface 18 aids in maintaining the seal. The pressure differential between the inside of the cap and the atmosphere can vary greatly. This depends in part on atmospheric conditions as well as how much depression is applied to the chamber before it resiliently returns to its normal position shown in FIG. 3. In some cases, the full repositioning of FIG. 3 is not achieved after compression of the side wall in application, but in all cases, some chamber vacuum or partial vacuum remains inside the cap. The interior chamber 12 can act as a reservoir if there is some leakage while the cap is in place, although this does not normally occur.

As previously noted, the skirt or flange size is such that it aids in positioning the flange in proper position over the urethral orifice and also maintaining the cap in place. The gripping portion is important for placement, particularly in older patients.

The differential in air pressure between the inside of the cap and the atmosphere is difficult to determine. In many cases, the air pressure differential may be as little as 1 psi or can be 2–5 psi or 6–10 psi or more. Preferably, the pressure is applied by the depression of the cap and the expansion thereof towards its original shape since the walls are resiliently deformable. This can result in different amounts of pressure when even the same cap is used depending on how it is applied and how much depression occurs. Surprisingly, it has been found that even with small caps following the method of this invention, sufficient air pressure difference is obtained to maintain the cap in position and avoid urine flow.

Thus, a user can alleviate urinary incontinence, including but not limited to stress incontinence, by applying the cap over the urethral orifice using the labia spacing to help position the cap. Prior to contact with the body, the cap is resiliently depressed at the hand or finger gripping portion and the encircling flange is brought into contact with the skin surrounding the orifice opening. The body contacting portion of the flange has been previously treated with AQUAPHOR® ointment or an adhesive as previously described. Slight pressure on the skin and release of the pressure deforming the cap causes a suction within the cap and provides the air pressure difference on the outside of flange 13 and intermediate flange 14 that maintains the cap in place on the body and closes the meatus as shown in FIG. 6. There can be a very slight elongation of the urethra reducing the inner diameter of the urethra, facilitating closure of the meatus. Any structure that provides a closure of the meatus to urine flow, yet allows comfort in use and ease of reuse, can provide the advantages of this invention. These advantages can be obtained by the device 10 acting solely externally of the body without any part thereof entering the body of a user. The cap remains comfortably in place and is flexible along the intermediate and outer flanges so as to move and flex with movement of the adjacent tissue. The cap can be easily removed to allow voiding when desired. In some cases, the cap can merely be pulled off the skin although a slight depression of the finger gripping portion is desired to alleviate the pressure difference first. The device is comfortable in use, can be easily applied by a majority of patients and has been found to prevent urinary leakage and thus alleviate urinary incontinence in women, including stress urinary incontinence.

In the preferred embodiment, the cap is packaged in a surrounding clear plastic container or envelope. This maintains the cleanliness of the cap prior to usage. Such envelopes are known in the art and can comprise thin plastic films which can be see through or opaque. Other conventional packages can be used to store and transport the urethral cap to maintain cleanliness. In some cases, a plurality of caps can be packaged in a single package or no package need be used. In some cases, the caps of this invention can be sterilized. Preferably, the caps 10 of this invention are manufactured and packaged under and meeting the FDA's Quality System as well as ISO 9000 standards to provide cleanliness, manufacturing quality and lot control. Thus, contamination, including bacterial contamination, is minimized.

The urinary caps of this invention can be sterilized to reduce the risk of infection or irritation to the skin. Sterilization is not required since the device is external to the body and does not have any component passing within the urethra.

It has been found that caps of this type are useful for long periods of time and maintain the contact with the skin in sealing arrangement for periods of 2 to 6 hours or more in some cases.

Figure 8:
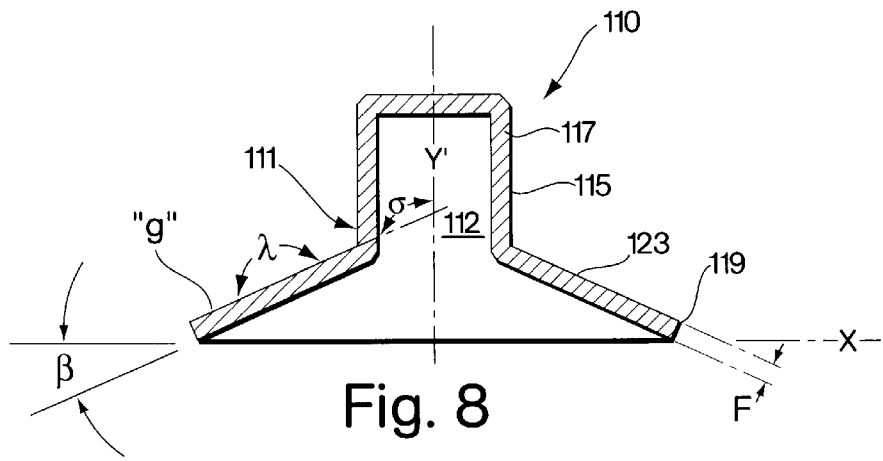
FIG. 8 is a cross-sectional side of a second preferred embodiment of a urethral cap according to the present invention, showing the same view as FIG. 3 of the first embodiment.

Turning now to another embodiment of this invention as shown in FIG. 8, an improved urethral cap 110 is illustrated in cross-section through a central axis Y'. In this embodiment of the urethral cap, all parts which are the same, or similar to, corresponding parts in the embodiment 10 are noted with the same two last numbers, but preceded by the numeral "1". The cap 110 includes a body 111 defining an interior chamber 112 and includes a gripping portion 117 having a cylindrical wall 115, as previously described. However, flange 123 which is preferably integrally molded with and extends from wall 115 is a single, unitary flange, which includes a body contacting surface having a continuous curvature in the present embodiment.

Flange 123 preferably has a thickness "f", is concentric about longitudinal axis Y' and extends an angle a with respect thereto. The thickness, "f" is preferably constant from first end 122 to outer edge 119, and is in the range of approximately 0.125 to 2 millimeters, with "f" being approximately 0.76 millimeters for the present embodiment. Alternately thickness "f" may be tapered, or decreasing in thickness from first end 122 adjacent wall 115 to outer edge 119. Angle a preferably ranges from approximately 55 degrees to 170 degrees, and is approximately 120 degrees in the embodiment of FIG. 8. The ability to utilize a single flange 123 in place of intermediate flange 14 and outer flange 13 results from both the positioning of the device when applied to a patient, i.e., as shown in FIG. 6. and described below, and further due to the thinness of flange 123. As shown in FIG. 6, when the urethral cap 10 is applied to a patient, angles θ and β (FIG. 3) become somewhat blended relative to the vertical axis Y, thereby forming a non-continuous curved surface, "c", with an angle λ disposed between intermediate flange 14 and outer flange 13. In prior art devices this angle was less than 180 degrees due, at least in part, to the thickness of the flanges. The thin nature and hence increased flexibility of the flanges of the present embodiment combined with the tendency of the flanges to merge when positioned, allows the flanges to be molded as a single flange 123 having an uninterrupted, continuous surface "g", rather than two flanges 13, 14 angled with respect to one another. In the present embodiment the continuous surface "g" is frustroconical, and may be defined by angle λ which, for the embodiment of FIG. 8, is equal to 180 degrees, thereby merging flanges 13 and 14 into a single, continuous frustroconical flange.

Figure 9:
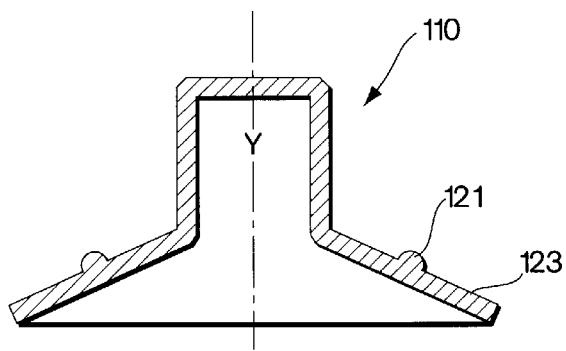
FIG. 9 is a cross-sectional side view of a modification of the embodiment of FIG. 8, further including a strengthening ridge but otherwise identical to the embodiment of FIG. 8.
Figure 10:
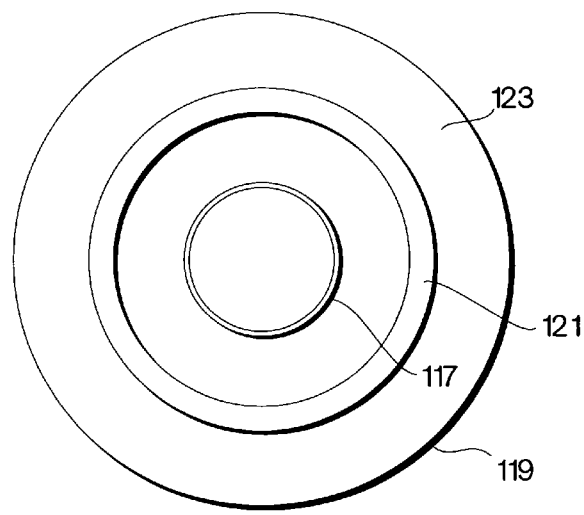
FIG. 10 is a top view of the embodiment of FIG. 9.
Figure 11:
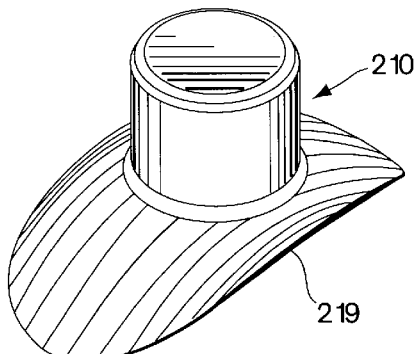
FIG. 11 is a perspective view of a third preferred embodiment of a urethral cap according to the present invention.
Figure 12:
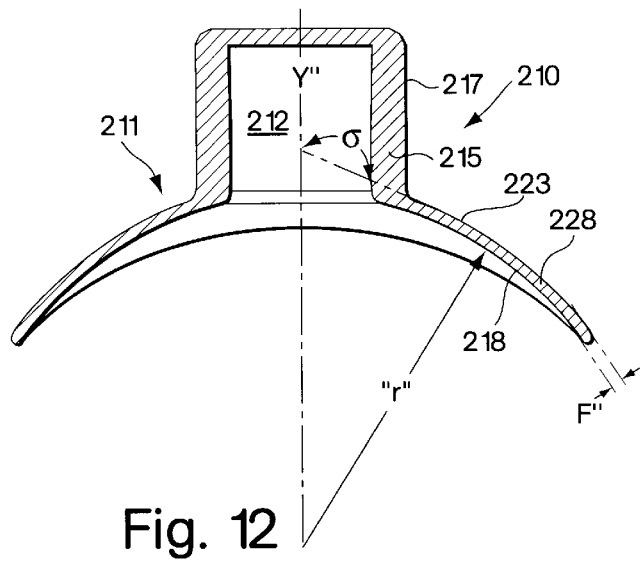
FIG. 12 is a cross-sectional, side view of the embodiment of FIG. 11.
Figure 14:
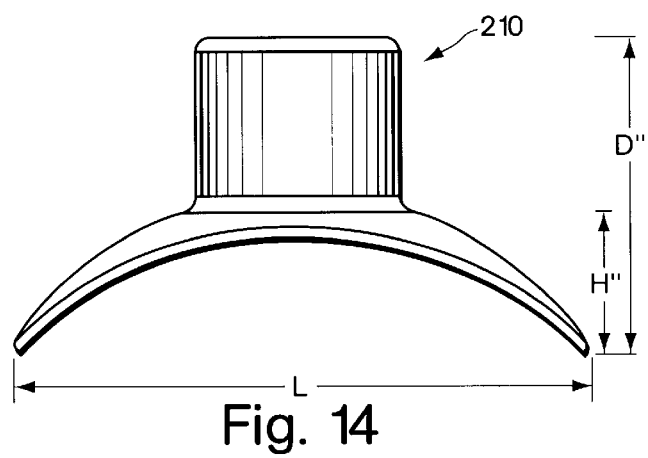
FIG. 14 is a side view of the embodiment of FIG. 11.

Referring now to FIGS. 9 and 10, when utilizing a single flange 123 it may be desired to include a strengthening ring or ridge 121 preferably disposed circumferentially thereabout. As shown in FIGS. 9 and 10 ridge 121 is preferably continuous, but may alternately be non-continuous and may be disposed about the edge of flange 123 instead of at an inward position therefrom. Ridge 121 provides additional structural support to flange 123 10 without compromising the flexibility of the flange or the continuous nature of the underlying curvature "g". Structural support may be especially useful if flange 123 is very thin, for example below 0.5 millimeters.

For the embodiment of FIGS. 8 and 9, it is preferred that the diameter A' be within the same range as previously described for diameter A. Likewise, it is preferred that the height D' of the device is within the same range as previously described for diameter D. All dimensions of gripping portion 117 may be the same, or substantially similar to, the dimensions for gripping portion 117. Distance H' which defines in part the interior chamber is preferably approximately 4.75 millimeters in the present embodiment but can vary substantially. As previously described, the dimensions of the device can vary greatly, as will be appreciated by one of skill in the art. In all embodiments of the invention, silicone rubber as previously described is the preferred embodiment.

In use, the device of FIGS. 8 and 9 operates to close the meatus as previously described with respect to the embodiment of FIG. 1. Flange 123 contacts the skin or tissue immediately surrounding the meatus in the same manner as described hereinabove with respect to flanges 13 and 14, the skin surrounding the meatus being compressed by the air pressure difference and forming a seal with the cap 110. As with the embodiment of FIG. 1, sealing material is preapplied to body contacting surface 118 of flange 123 to aid in maintaining the seal.

Referring now to FIGS. 11–15, there is illustrated another embodiment of an improved urethral cap 210 according to the present invention. In this embodiment of the urethral cap, all parts which are the same, or similar to, corresponding parts of embodiments 10 and 110 are noted with the same two last numbers, but preceded by the numeral "2". The cap 210 includes a body 211 defining an interior chamber 212 and includes a gripping portion 217 having a cylindrical wall 215, as previously described. However, flange 223 which is preferably a single, continuous, unitary flange integrally molded with wall 115, has a generally oval, or elliptical shape and is preferably symmetrical about longitudinal axis Y". The generally eliptical shape of flange 223 closely approximates a female's natural contours extending between the vagina and clitoris. This provides the user with increased comfort over an extended period of time.

The embodiment of FIGS. 11–15 includes a concave body contacting surface 218, and a convex outer wall surface 228, opposite the body contacting surface 218. Flange 223 extends at an angle a which is preferable in the range of approximately 90 degrees to 170 degrees, and is approximately 120 degrees in the embodiment of FIG. 11. The curvature of flange 223 is defined by a radius, "r", which is at least approximately 12.7 millimeters, and can approach infinity if it is desired to flatten the curvature to nearly a straight line. As with the embodiment of FIG. 8, flange 223 has a thickness, f", which is preferably constant and is in the range of approximately 0.125 to 2.0 millimeters, and is preferably approximately 0.64 millimeters for the present embodiment. Alternately, thickness f" may be tapered, or decreasing in thickness from wall 215 to outer edge 219 of flange 223. Although not illustrated, it may be desired to include a strengthening ring or ridge about flange 223 to provide support thereto. As with the previous embodiments the ridge is preferably continuous, but may alternately be non-continuous and may be disposed about the edge of flange 123 or, alternately, at an inward position therefrom.

For the embodiment of FIGS. 11–15, it is preferred that the length L be in the range of approximately 2.0 to 3.5 centimeters with approximately 3 centimeters being used in the preferred embodiment. Width W, which is taken along the widest point of flange 223, is preferably in the range of approximately 1.5 centimeters to 3.0 centimeters with approximately 2.0 centimeters being preferred. Because flange 223 is generally eliptical in shape, the width decreases from the center toward either end of flange 223. It is prefered that the height D" of the device be approximately 1 to approximately 2 centimeters, and is approximately 1.78 centimeters in the present embodiment. All dimensions of gripping portion 217 may be the same, or substantially similar to, the dimensions for gripping portion 117. Distance H" which defines in part the interior chamber is preferably approximately 1 centimeter in the present embodiment, but can vary substantially. As previously described, the dimensions of the device can vary greatly, as will be appreciated by one of skill in the art.

Figure 13:
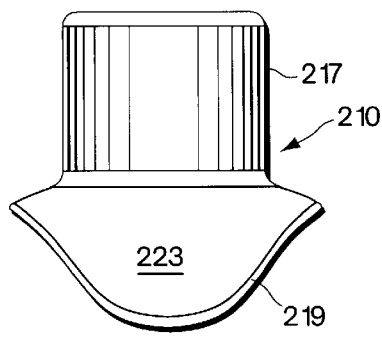
FIG. 13 is a front view of the embodiment of FIG. 11.
Figure 13A:
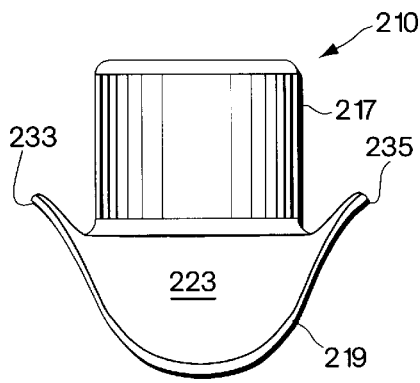
FIG. 13a is a front view of the embodiment of FIG. 11, after positioning on the user.
Figure 15:
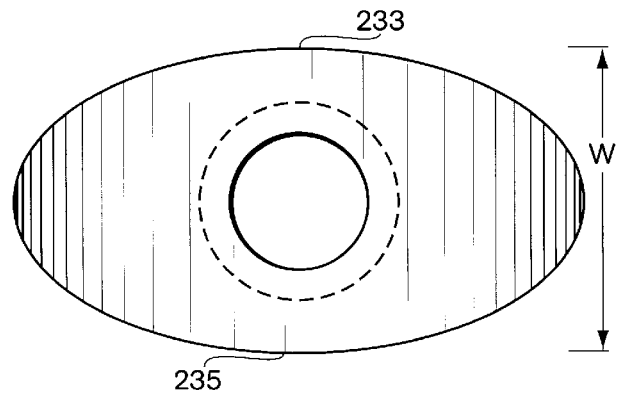
FIG. 15 is a top view of the embodiment of FIG. 11.

In use, the device 210 operates to close the meatus as previously described with respect to device 10 and device 110. Flange 223 contacts the skin or tissue immediately surrounding the meatus in the same manner as described hereinabove with respect to flanges 13 and 14, the skin surrounding the meatus being compressed by the air pressure difference and forming a seal with the cap 110. As with the previous embodiments, sealing material is preapplied to body contacting surface 218 of flange 223 to aid in maintaining the seal. Because the shape of flange 223 more closely approximates the shape of a woman when positioned between the labia from the clitoris to the vagina, the device 210 is easier to position for some users, than circular embodiments and has a more comfortable fit. When positioned, the sides 233 and 235 of flange 223 may turn upwardly into the shape illustrated in FIG. 13a. The "cowboy hat shape" the device assumes in FIG. 13a is due primarily to the contours of the female anatomy, the shape of the device and the thinness of the flange. Alternately, sides 233 and 235 may be initially molded in this upward turning direction.

Figure 16:
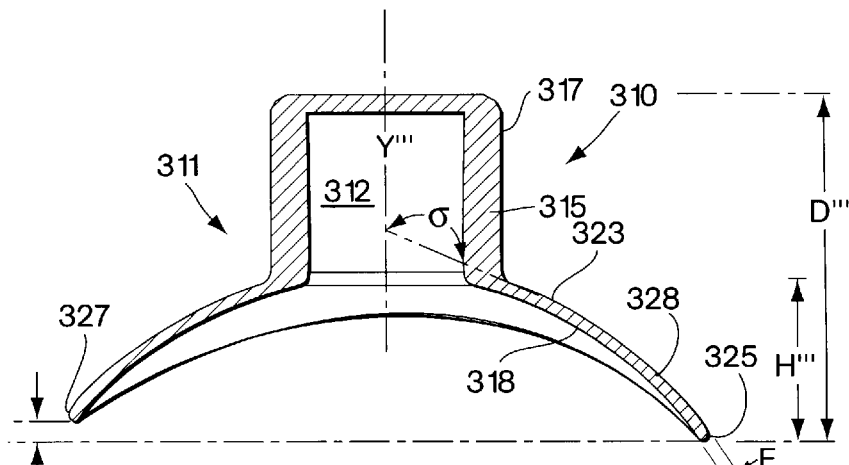
FIG. 16 is a cross-sectional side view of a fourth preferred embodiment of a urethral cap according to the present invention, showing the same view as FIGS. 3, 8 and 12.
Figure 17:
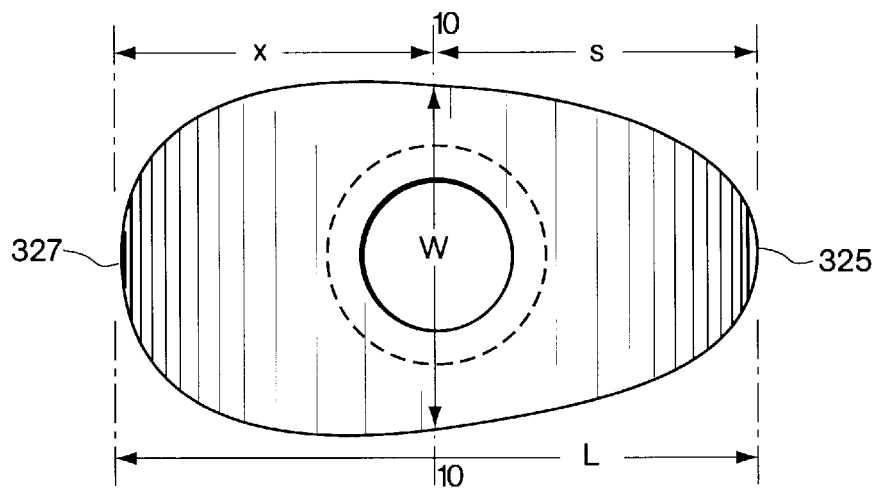
FIG. 17 is a top view of the embodiment of FIG. 16.
Figures 18, 19:
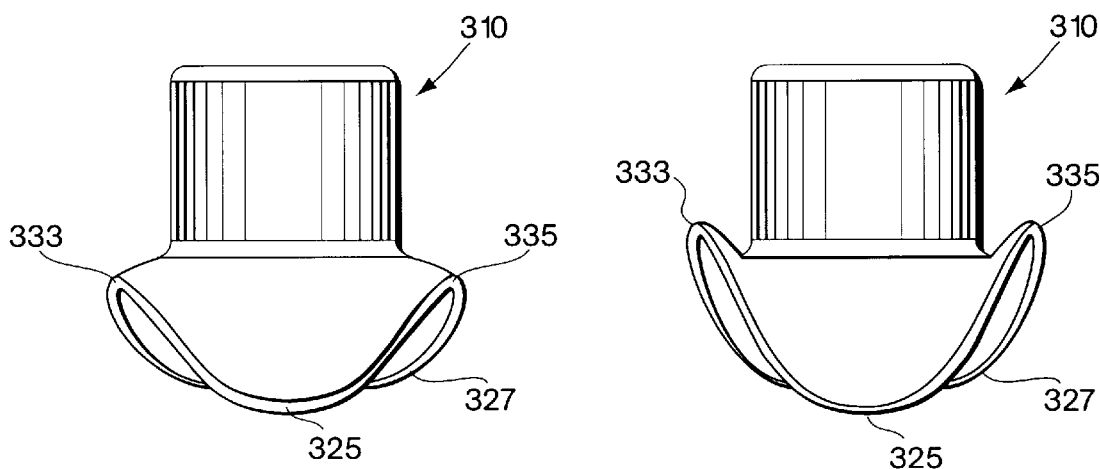
FIG. 18 is a front view of the embodiment of FIG. 16.
FIG. 19 is a front view of the embodiment of FIG. 16, after positioning on the user.

Referring now to FIGS. 16–18, there is illustrated another embodiment of an improved urethral cap 310 according to the present invention. In this embodiment of the urethral cap, all parts which are the same, or similar to, corresponding parts of embodiments 10, 110 and 210 are noted with the same two last numbers, but preceded by the numeral "3". The cap 310 includes a body 311 defining an interior chamber 312 and includes a gripping portion 317 having a cylindrical wall 315, as previously described. However, flange 323 which is preferably a single, unitary flange integrally molded with wall 315, has a generally "egg" shape and is therefore non-symmetrical about longitudinal axis Y'". The "egg" shape of flange 323 likewise closely approximates a female's natural contours extending from the vagina to the clitoris, with first end 325 being disposed adjacent the clitoris and second end 327 being disposed adjacent the vagina in use. This provides the user with increased comfort, as the area between the labia adjacent the clitoris is smaller than the area between the labia adjacent the vagina, in the majority of women.

The embodiment of FIGS. 16–18 includes a concave body contacting surface 318, and a convex outer wall surface 328, opposite the body contacting surface 318. Flange 323 extends at an angle σ which is preferable in the range of approximately 90 degrees to 170 degrees, and is approximately 120 degrees in the embodiment of FIG. 16. As with the embodiment of FIG. 11, the curvature of flange 323 is defined by a radius, "r", which is at least approximately 12.7 millimeters, and can approach infinity if it is desired to flatten the curvature to nearly a straight line. Flange 323 likewise has a thickness, f", which is preferably constant and is in the range of approximately 0.125 to 2 millimeters, and is preferably approximately 0.64 millimeters for the present embodiment. Alternately, thickness f" may be tapered, or decreasing in thickness from wall 315 to outer edge 319 of flange 323. Although not illustrated, it may be desired to include a strengthening ring or ridge about flange 323 to provide support thereto. As with the previous embodiments the ridge is preferably continuous, but may alternately be non-continuous and may be disposed about the edge of flange 323 or, alternately, at an inward position therefrom.

For the embodiment of FIGS. 11–15, it is preferred that the overall length L be in the range of approximately 2 to 3.5 centimeters with approximately 3 centimeters being used in the preferred embodiment. The length "s" of flange 323 from axis Y to first end 325 is preferably from approximately 1 to approximately 2 centimeters and is 1.65 centimeters in the present embodiment, while the length "x" of flange 323 from axis Y to second end 327 is preferably 1.35 centimeters in the present embodiment. Since the length from axis Y to the second end 327 is shorter than to first end 325, when viewed from the side, second end 327 is 1 millimeter above first end 325, as shown by "m" in FIG. 16. This also more closely approximates the natural position of the clitoris with respect to the vagina. Width W, which is taken along line 10—10 of flange 323, is preferably in the range of approximately 1.5 centimeters to 3.0 centimeters with approximately 2.0 centimeters being preferred. Because flange 323 is generally egg-shape, the width decreases from the center toward first end 325 and preferably increases toward the second end 327 of flange 323. It is prefered that the height D'" of the device be approximately 1 to approximately 2 centimeters, and is 1.78 centimeters in the present embodiment. All dimensions of gripping portion 317 may be the same, or substantially similar to, the dimensions for gripping portion 317. Distance H'" which defines in part the interior chamber is preferably approximately 1 centimeter in the present embodiment, but can vary substantially. As previously described, the dimensions of the device can vary greatly, as will be appreciated by one of skill in the art.

In use, the device 310 operates to close the meatus as previously described with respect to device 10, 110 and 210. Flange 323 contacts the skin or tissue immediately surrounding the meatus in the same manner as described hereinabove, the skin surrounding the meatus being compressed by the air pressure difference and forming a seal with the cap 310. As with the previous embodiments, sealing material is preapplied to a body contacting surface 318 of flange 323 to aid in maintaining the seal. Because the shape of flange 323 more closely approximates the shape of a woman when positioned between the labia from the clitoris to the vagina, the device 310 is easier to position than circular embodiments and has a more comfortable fit. As with the device of FIG. 11, when positioned, the sides 333 and 335 of flange 323 may turn upwardly into the shape illustrated in FIG. 19.

It will be understood that various modifications may be made to the embodiments disclosed herein. For example, all angles and measurements are approximate and may be varied by one of skill in the art. Therefore, the above description should not be construed as limiting, but merely as exemplifications of a preferred embodiment. Those skilled in the art will envision other modifications within the scope spirit of the invention.

What is claimed is:

1. A urethral cap adapted to alleviate urinary incontinence when positioned on the body of a user, between the labia and over the urethra, the cap comprising:
    a body portion defining an interior chamber, said chamber providing a vacuum therein adapted to hold said urethral cap in contact with the body of the user;
    a single flange supported by said body portion and having a body contacting surface, said single flange acting as a sealing surface when said single flange encircles the urethra, wherein movement of the body of the user adjacent the flange causes corresponding movement of the flange while maintaining a seal around the urethra;
    a strengthening ridge disposed at least partially about and supported by said single flange the strengthening ridge providing support to said single flange when in place over the urethra.

2. A urethral cap in accordance with claim 1, wherein said strengthening ridge is supported along an outer edge of said single flange.

3. A urethral cap in accordance with claim 2, wherein said strengthening ridge is continuous about the outer edge.

4. A urethral cap adapted to alleviate urinary incontinence when encircling the urethra of a user, the cap comprising:
    a gripping portion having at least one wall adapted for use in placing the cap externally over the urethra;
    a body portion defining an interior chamber for establishing a pressure differential between the urethral cap and the atmosphere adapted to aid in maintaining the cap in position attached to the body;
    at least one flexible flange supported by the gripping portion, the at least one flange having a body contacting surface adapted to act as a sealing surface with the body of the user; and
    a strengthening ridge disposed at least partially about and supported by said at least one flange, the strengthening ridge providing support to the at least one flange when in place over the urethra while allowing the flange to remain flexible.

5. A urethral cap in accordance with claim 4, wherein said at least one flexible flange includes an intermediate flange extending from the gripping portion and an outer flange supported by the intermediate flange.

6. A urethral cap in accordance with claim 4, wherein said intermediate flange has a tapered thickness.

7. A urethral cap in accordance with claim 4, wherein said outer flange has a constant thickness.

8. A urethral cap in accordance with claim 7, wherein the wall of said gripping portion has a constant thickness.

9. A urethral cap in accordance with claim 8, wherein the thickness of said intermediate flange tapers from approximately the thickness of the gripping portion to the thickness of the outer flange.

10. A urethral cap in accordance with claim 7, wherein said outer flange has a constant thickness of less than approximately 0.75 millimeters.

11. A urethral cap in accordance with claim 4, wherein the at least one flange is a single flange extending from said gripping portion.

12. A urethral cap in accordance with claim 11, wherein said single flange has a constant thickness.

13. A urethral cap according to claim 12, wherein said single flange has a thickness in the range of approximately 0.125 to approximately 0.75 millimeters.

14. A urethral cap according to claim 13, wherein the thickness of said single flange is less than approximately 0.5 millimeters, but is at least approximately 0.125 millimeters.

15. A urethral cap in accordance with claim 4, wherein the strengthening ridge is supported along an outer edge of said at least one flange.

16. A urethral cap in accordance with claim 5, wherein the strengthening ridge is supported along an outer edge of said outer flange.

17. A urethral cap in accordance with claim 11, wherein the strengthening ridge is supported along an outer edge of said single flange.

18. A urethral cap in accordance with claim 4, wherein said strengthening ridge is continuous about said at least one flange.

19. A urethral cap adapted to alleviate urinary incontinence, when applied over the meatus of the body of a user, the cap comprising:

an at least partially deformable cap body having a gripping portion, a chamber defined by said cap body, the chamber sized to allow for reciprocal resilient deformation of said cap body adapted to provide a vacuum therein to hold said urethral cap on the body of a user, in contact with tissue surrounding the meatus to close the meatus of the user;

at least one flange supported by said gripping portion, said at least one flange having a body contacting surface adapted to act as a sealing surface when in contact with the body of the user, the at least one flange having a thickness of less than approximately 0.4 millimeters adapted to provide the flange with pliability that closely approximates the pliability of the surrounding tissue; and at least one strengthening ridge disposed at least partially about and supported by said at least one flange.

20. A urethral cap in accordance with claim 19, wherein said at least one strengthening ridge includes a plurality of concentric strengthening ridges.

21. A urethral cap in accordance with claim 19, wherein said strengthening ridge is continuous about the outer edge.

22. In a female incontinence device having a hand gripping portion defining a vacuum chamber and an outwardly extending flange having a body contacting surface adapted for use with a sealing material, the improvement comprising;

the said outwardly extending flange having a shape selected from the group consisting of a generally elliptical shape and an egg shape;

the outwardly extending flange having a thickness less than approximately 0.5 millimeters and a strengthening ridge disposed about the flange to provide support thereof; and said body contacting surface being concave.

* * * * *